United States Patent
Yoda

(10) Patent No.: US 9,924,876 B2
(45) Date of Patent: Mar. 27, 2018

(54) OBJECT INFORMATION ACQUIRING APPARATUS AND METHOD OF CONTROLLING SAME

(71) Applicant: CANON KABUSHIKI KAISHA, Tokyo (JP)

(72) Inventor: Haruo Yoda, Nishitama-gun (JP)

(73) Assignee: Canon Kabushiki Kaisha, Tokyo (JP)

( * ) Notice: Subject to any disclaimer, the term of this patent is extended or adjusted under 35 U.S.C. 154(b) by 1028 days.

(21) Appl. No.: 14/207,881

(22) Filed: Mar. 13, 2014

(65) Prior Publication Data

US 2014/0296689 A1    Oct. 2, 2014

(30) Foreign Application Priority Data

Mar. 29, 2013   (JP) .................. 2013-073462

(51) Int. Cl.
*A61B 8/00* (2006.01)
*A61B 5/00* (2006.01)
*G01N 29/22* (2006.01)

(52) U.S. Cl.
CPC ........... *A61B 5/0095* (2013.01); *G01N 29/22* (2013.01)

(58) Field of Classification Search
CPC .............................. A61B 5/0095; G01N 29/22
USPC ................................................. 600/407–480
See application file for complete search history.

(56) References Cited

U.S. PATENT DOCUMENTS

| 5,713,356 | A   | *   | 2/1998  | Kruger ............. A61B 5/0091 600/407 |
| 6,979,292 | B2  |     | 12/2005 | Kanayama et al. ......... 600/437 |
| 9,370,307 | B2  | *   | 6/2016  | Wada ................... A61B 5/0095 |
| 2011/0098550 | A1 |     | 4/2011  | Yoda ............................ 600/407 |
| 2011/0208057 | A1 | *  | 8/2011  | Oikawa ................ A61B 5/0095 600/443 |
| 2012/0044785 | A1 |    | 2/2012  | Yoda et al. ..................... 367/92 |
| 2012/0257472 | A1 |    | 10/2012 | Yoda .................................. 367/7 |
| 2012/0281902 | A1 |    | 11/2012 | Oikawa et al. ............... 382/131 |
| 2012/0314534 | A1 |    | 12/2012 | Yoda et al. ........................ 367/7 |

(Continued)

FOREIGN PATENT DOCUMENTS

| JP | A 2001-507952 | 6/2001 |
| JP | A 2005-021380 | 1/2005 |

(Continued)

OTHER PUBLICATIONS

Office Action dated Feb. 28, 2017 in counterpart Japanese patent application 2013-073462, with machine translation.

*Primary Examiner* — Sanjay Cattungal
(74) *Attorney, Agent, or Firm* — Fitzpatrick, Cella, Harper & Scinto

(57) ABSTRACT

Provided is an object information acquiring apparatus including a probe having a plurality of receiving elements that are arrayed along a first direction and receive an acoustic wave generated from an object irradiated with light from a light source and converting the acoustic wave into an electrical signal, a scanner that moves the probe in the first direction, a controller, and a generator that generates image data of inside of the object based on the electrical signal. The controller controls the apparatus such that light is emitted each time the probe is moved by a distance that is either (n+1/k) times or (n−1/k) times an array pitch between the receiving elements, where n is an integer of 1 or more and k is an integer of 2 or more.

23 Claims, 15 Drawing Sheets

(56) References Cited

U.S. PATENT DOCUMENTS

| | | | |
|---|---|---|---|
| 2013/0116536 A1 | 5/2013 | Sato | 600/407 |
| 2013/0116537 A1 | 5/2013 | Sato | 600/407 |
| 2013/0116539 A1 | 5/2013 | Nagao | 600/407 |
| 2013/0131487 A1 | 5/2013 | Nagao | 600/407 |

FOREIGN PATENT DOCUMENTS

| | | |
|---|---|---|
| JP | A 2008-264218 | 11/2008 |
| JP | A 2010-022812 | 2/2010 |
| JP | A 2011-125571 | 6/2011 |
| WO | WO 98/014118 A | 4/1998 |
| WO | WO 98/141188 A | 4/1998 |
| WO | WO 2012/108143 | 8/2012 |
| WO | WO 2012/153479 | 11/2012 |
| WO | WO 2012/153481 | 11/2012 |

* cited by examiner

| No. | NUMBER OF ARRAYED ELEMENTS N | MOVING DISTANCE (n ± 1/k) | MOVING DISTANCE / EMISSION FREQUENCY |
|---|---|---|---|
| 1 | 3 | 1 − 1/4 | 0.75 × d |
| 2 | 5 | 1 + 1/4 | 1.25 × d |
| 3 | 7 | 2 − 1/4 | 1.75 × d |
| 4 | 9 | 2 + 1/4 | 2.25 × d |
| 5 | 11 | 3 − 1/4 | 2.75 × d |
| 6 | 13 | 3 + 1/4 | 3.25 × d |
| 7 | 15 | 4 − 1/4 | 3.75 × d |
| 8 | 17 | 4 + 1/4 | 4.25 × d |
| 9 | 19 | 5 − 1/4 | 4.75 × d |
| 10 | 21 | 5 + 1/4 | 5.25 × d |
| 11 | 23 | 6 − 1/4 | 5.75 × d |
| 12 | 25 | 6 + 1/4 | 6.25 × d |

FIG. 5

| No. | DIVISION NUMBER k | MOVING DISTANCE (n ± 1/k) | MOVING DISTANCE / EMISSION FREQUENCY |
|---|---|---|---|
| 1 | 2 | 6 + 1/2 | 6.5 × d |
| 2 | 3 | 4 + 1/3 | 4.333 × d |
| 3 | 4 | 3 + 1/4 | 3.25 × d |
| 4 | 6 | 2 + 1/6 | 2.167 × d |

FIG. 7

```
n0:=Floor[(N+1)/k];
n1:=Floor[(N-1)/k];
If n0>n1 then
  OPTIMAL MOVING DISTANCE := (n0-1/k);
else
  OPTIMAL MOVING DISTANCE := (n1+1/k);
endif;
```

FIG. 11

OBJECT INFORMATION ACQUIRING APPARATUS AND METHOD OF CONTROLLING SAME

BACKGROUND OF THE INVENTION

Field of the Invention

The present invention relates to an object information acquiring apparatus and a method of controlling the apparatus.

Description of the Related Art

Photoacoustic imaging is a method of visualizing the three-dimensional structure of the inside of an object by irradiating the object with light such as laser pulses and detecting photoacoustic waves that are generated by thermal expansion. With the use of light of various wavelengths, a distribution of a substance that absorbs a particular wavelength, such as hemoglobin or glucose in blood, can be visualized. As the method enables non-invasive detection of neovascular vessels that are characteristic of a tumor, it is attracting attention as means of early detection of breast cancer.

A specific procedure of a conventional photoacoustic imaging method is disclosed in Japanese Translation of PCT Application No. 2001-507952, for example, as follows:

(Step 1) A probe with two-dimensional arrays of receiving elements (2D probe) that convert an acoustic wave into an electrical signal is placed on the surface of an object, and the object is irradiated with single pulsed electromagnetic energy.

(Step 2) Signals received by each receiving element are sampled and stored, from immediately after the irradiation with electromagnetic energy.

(Step 3) A delay time for an acoustic wave to propagate from a point of interest in the object to the position of each receiving element is calculated, and the delay time is added to the corresponding received signal to obtain the intensity of the image data of the point of interest.

(Step 4) Step 3 is repeated for each point of interest to be visualized.

Japanese Patent Application Laid-open No. 2005-21380 discloses a method of reconstructing an image from both of a photoacoustic image and a normal ultrasound image using a common probe with a one-dimensional array of receiving elements (1D probe). To reconstruct a three-dimensional image of a wide area with this 1D probe, the probe needs to be moved mechanically in a direction orthogonal to the direction in which the receiving elements are arranged.
Patent Literature 1: Japanese Translation of PCT Application No. 2001-507952
Patent Literature 2: Japanese Patent Application Laid-open No. 2005-21380

SUMMARY OF THE INVENTION

To improve the quality of a three-dimensional reconstructed image with the use of a photoacoustic imaging method, as is known, it is effective to use photoacoustic signals based on photoacoustic waves that are received at short intervals.

The present invention was made in view of the circumstances described above, its object being to provide a photoacoustic imaging technique that allows for detection of photoacoustic waves at an interval corresponding to a distance that is eventually shorter than the array pitch between receiving elements.

The present invention provides an object information acquiring apparatus, comprising: a light source;
a probe having a plurality of receiving elements arrayed along a first direction, the receiving elements receiving an acoustic wave generated from an object when the object is irradiated with light from the light source, and converting the acoustic wave into an electrical signal;
a scanner moving the probe in the first direction;
a controller controlling the light source and the scanner;
an A/D converter converting the electrical signal converted by the receiving elements into a digital signal;
a memory storing the digital signal converted by the A/D converter; and
a generator generating image data of inside of the object based on the digital signal stored in the memory, wherein
the controller controls the apparatus such that light is emitted from the light source each time the probe is moved by a distance that is either $(n+1/k)$ times or $(n-1/k)$ times an array pitch between the receiving elements, where n is an integer of 1 or more and k is an integer of 2 or more.

The present invention also provides an object information acquiring apparatus, comprising: an ultrasound transmitter;
a probe having a plurality of receiving elements arrayed along a first direction, the receiving elements receiving an echo of a sound wave transmitted from the ultrasound transmitter to an object and reflected from the object, and converting the echo wave into an electrical signal;
a scanner moving the probe in the first direction;
a controller controlling the ultrasound transmitter and the scanner;
an A/D converter converting the electrical signal converted by the receiving elements into a digital signal;
a memory storing the digital signal converted by the A/D converter; and
a generator generating image data of inside of the object based on the digital signal stored in the memory, wherein
the controller controls the apparatus such that ultrasound is transmitted from the ultrasound transmitter each time the probe is moved by a distance that is either $(n+1/k)$ times or $(n-1/k)$ times an array pitch between the receiving elements, where n is an integer of 1 or more and k is an integer of 2 or more.

The present invention also provides a method of controlling an object information acquiring apparatus that includes a light source, a probe having a plurality of receiving elements arrayed along a first direction, a scanner moving the probe in the first direction, a controller controlling the light source and the scanner, an A/D converter, a memory, and a generator, the method comprising:
a reception step of receiving an acoustic wave generated from an object when the object is irradiated with light from the light source and converting the acoustic wave into an electrical signal by the plurality of receiving elements;
an A/D conversion step of converting the electrical signal converted in the previous step into a digital signal by the A/D converter;
a storage step of storing the digital signal converted in the A/D conversion step in the memory; and
a generation step of generating image data of inside of the object based on the digital signal stored in the storage step by the generator, wherein in the reception step, the controller controls the apparatus such that light is emitted from the light source each time the probe is moved by a distance that is either (n+1/k) times or (n−1/k) times an array pitch between the receiving elements, where n is an integer of 1 or more and k is an integer of 2 or more.

The present invention can provide a photoacoustic imaging technique for detecting photoacoustic waves at an interval corresponding to a distance that is eventually shorter than the array pitch between receiving elements.

Further features of the present invention will become apparent from the following description of exemplary embodiments with reference to the attached drawings.

BRIEF DESCRIPTION OF THE DRAWINGS

FIG. 5 is a table showing numbers N of arrayed elements and moving distances when inputting acoustic signals at a four times higher density;

FIG. 7 is a table showing moving distances when inputting acoustic signals with 13 elements at various densities;

FIG. 11 is a diagram for explaining a procedure of calculating a moving distance.

DESCRIPTION OF THE EMBODIMENTS

Figure 1:
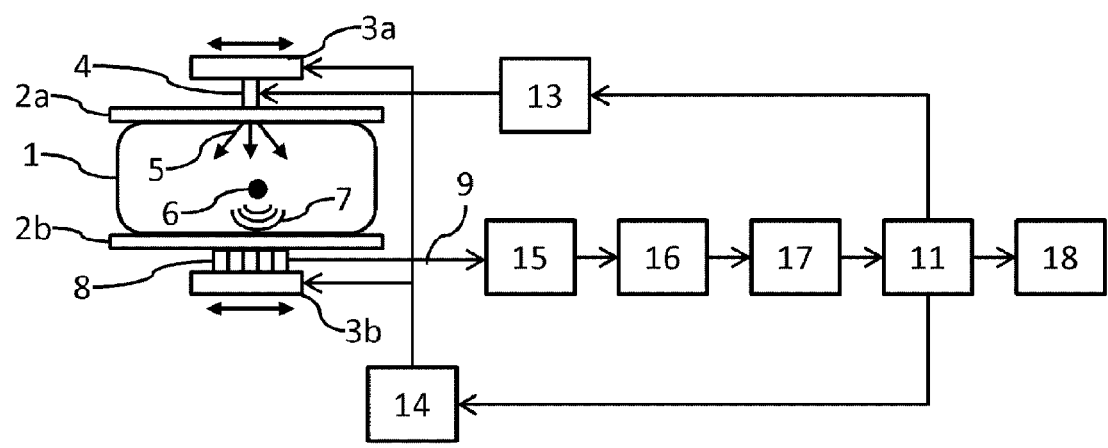
FIG. 1 is a diagram illustrating the configuration of a photoacoustic imaging apparatus.

Embodiments of the present invention will be hereinafter described in detail with reference to the drawings. It should be noted that it is not intended to limit the scope of this invention to the specifics given below, and the formulas and calculation procedures or the like described below in detail should be changed as required in accordance with the configurations and various conditions of the apparatus to which the invention is applied.

The object information acquiring apparatus of the present invention is an apparatus for acquiring information of an object as image data by receiving an acoustic wave that is generated inside the object when the object is irradiated with light (electromagnetic wave) by the photoacoustic effect and that propagates through the object. The object information acquiring apparatus may also be regarded as a photoacoustic imaging apparatus that visualizes the inside of an object. The object information thus acquired includes source distributions of acoustic waves generated by light irradiation, initial sound pressure distributions inside the object, or, light energy absorption density distributions, absorption coefficient distributions, or density distributions of tissue-forming substances, which are deduced from the initial sound pressure distributions. The tissue-forming substances may be, for example, blood components that indicate an oxygen saturation distribution or a distribution of oxyhemoglobin/deoxyhemoglobin concentration, or, fat, collagen, water, and the like.

The present invention can also be applied to an ultrasonic apparatus that generates image data by receiving ultrasound transmitted to and reflected from an object (ultrasound echo). In this case the object information represents a difference in acoustic impedance.

The acoustic waves referred to in the present invention are typically ultrasound waves, including elastic waves that are called sound waves or acoustic waves. An acoustic wave generated by the photoacoustic effect is referred to as a "photoacoustic wave", or a "light-induced ultrasound wave". The apparatus of the present invention receives an acoustic wave that is generated or reflected in, and propagated through, the object with an acoustic wave detector such as a probe.

An electrical signal based on such a photoacoustic wave will hereinafter be also referred to as a photoacoustic signal. Photoacoustic signals include an analog signal converted from a photoacoustic wave by a receiving element of a probe, or a digital signal obtained through amplification of, or A/D conversion from, an analog signal. "Acquiring a photoacoustic signal" refers to irradiating an object with light to generate a photoacoustic wave and inputting a resultant digital signal in a memory or the like.

(Image Quality Improvement Techniques)

In some methods of improving the quality of reconstructed three-dimensional images taken by photoacoustic imaging, as mentioned above, photoacoustic signals may be acquired at an interval corresponding to a distance that is eventually shorter than the array pitch between receiving elements of a two-dimensional probe, and used to reconstruct a three-dimensional image. Below, two methods of acquiring signals at an interval corresponding to a quarter of the array pitch d between the elements will be discussed.

The first method alternately repeats a first step of acquiring a photoacoustic signal at short intervals and a second step of moving the probe largely. In the first step, the probe is moved slightly by d/4 each time, and a photoacoustic signal is acquired once at each position, i.e., a total of four times. In the second step, the probe is moved just by the width of the probe.

In this way, photoacoustic signals can be acquired at a density that is four times higher than normally achieved in an examination area that is broader than the width of the probe. With this method, however, the moving speed of the probe is changed frequently, as the probe is moved at largely different rates in the first step and second step. The probe control is thus difficult, and signal acquisition at high speed is hard to accomplish.

The second method repeats mechanical scanning of the entire examination area four times. Each mechanical scanning is performed such that photoacoustic signal is received at positions offset by d/4. This can be accomplished by, for example, displacing the measurement starting position of the probe by d/4. The photoacoustic signal is acquired once each time the probe is moved by the width of the probe in each mechanical scanning.

This way, signals can be acquired at high speed while the probe is moved at constant speed. However, since the probe needs to be moved back and forth and so forth, the overall length of time required for the measurement is long. Another problem is that, since photoacoustic signals acquired at positions that are adjacent and displaced by d/4 are obtained at largely different timing, the precision of a resultant reconstructed image is degraded if the object is a living body that changes as time passes.

(Structure of and Scanning with the Probe of the Present Invention)

In the present invention, a probe that has regularly arrayed receiving elements is moved continuously in the direction of arrangement of the elements relative to the object. As the probe is moved continuously, photoacoustic waves are received to acquire photoacoustic signals. A three-dimensional image of the inside of the object is generated based on the signals.

It is assumed that the one-dimensional probe in Japanese Patent Application Laid-open No. 2005-21380 mentioned above is also moved continuously. However, unlike the present invention, the moving direction is orthogonal to the direction in which the receiving elements are arranged.

One problem of receiving photoacoustic waves while moving the probe continuously is that the probe position changes during the reception of photoacoustic waves. However, photoacoustic waves are received in a very short time of about 50 to 100 μs after the emission of light. Meanwhile, the repetition frequency of high power laser pulses is normally limited to a slow rate of about 100 ms. Thus the receiving elements are inevitably moved at low speed to match the slow emission rate. Therefore, even though the probe is continuously moved while detecting photoacoustic waves, the difference in position is effectively negligible, as compared to when the probe is paused to detect photoacoustic waves.

In the present invention, as the photoacoustic waves are received while the probe is moved continuously, not only the control of probe movement is made easy, but also the time required for positioning is omitted, so that photoacoustic signals can be acquired at high speed.

Embodiment 1

FIG. 1 is a diagram illustrating the overall configuration of a photoacoustic imaging apparatus. The photoacoustic imaging apparatus includes clamping plates 2a and 2b, moving tables 3a and 3b, a pulsed laser light source 4, a probe 8, a calculator 11, a laser light source control circuit 13, a moving table control circuit 14, an A/D conversion circuit 15, a memory circuit 16, an image reconstruction circuit 17, and a display device 18. The measurement target is an object 1 held between the clamping plates 2a and 2b. The object 1 contains a detection target 6 which is a light absorbing body such as hemoglobin. The pulsed laser light source 4 is arranged on the moving table 3a such as to be movable. Instead of moving the pulsed laser light source 4, an exit of light that is directed from an optical system to be emitted may be moved. The probe 8 is arranged on the moving table 3b such as to be movable.

When the object 1 is irradiated with light 5 from the pulsed laser light source 4 through the clamping plate 2a, the detection target 6 absorbs light energy and expands, whereby an acoustic wave (photoacoustic wave) 7 is generated. Part of the acoustic wave 7 is received by the receiving elements of the probe 8 through the clamping plate 2b and converted into an electrical signal (photoacoustic signal). If there are a plurality of detection targets 6 inside the object, acoustic waves generated from each of them are superimposed and received by the probe 8.

Signals received by the receiving elements of the probe 8 are stored temporarily in the memory circuit. The distribution of detection targets inside the object is then reconstructed as a three-dimensional image based on the stored signals. Various known techniques (such as delay-and-sum beam forming) can be used for the reconstruction process.

When the object is larger than the arrayed area of receiving elements of the probe, the pulsed laser light source 4 and the probe 8 are moved by the moving tables 3a and 3b in synchronism with each other, and photoacoustic signals are acquired at each position. In this case, a partial three-dimensional image may be reconstructed each time based on the obtained photoacoustic signals, or, the photoacoustic signals may be stored in the memory circuit until after photoacoustic signals have been obtained from the entire region of the measurement target, to reconstruct an image.

The calculator 11 is the controller of the entire apparatus. The calculator 11 starts up the laser light source control circuit 13 at the same time when instructing the moving table control circuit 14 to start up. The moving table control circuit 14 and the laser light source control circuit 13 control the pulsed laser light source 4 and the moving tables 3a and 3b such that light is emitted when the tables have reached a predetermined position. Each of the receiving elements in the probe 8 receives a photoacoustic wave generated from a detection target 6 and converts it into a photoacoustic signal 9. The photoacoustic signal 9 is converted into a digital equivalent by the A/D conversion circuit 15 and stored in the memory circuit 16. The calculator 11 corresponds to the "controller" of the present invention. The moving table control circuit 14 controls the moving tables 3a and 3b, and these together form the "scanner" of the present invention. The A/D conversion circuit 15 corresponds to the "A/D converter" of the present invention. The memory circuit 16 corresponds to the "memory" of the present invention.

The signals received and stored in the memory circuit 16 are read out at proper timing by the image reconstruction circuit 17 and used for the reconstruction process to produce a three-dimensional image. The calculator 11 reads out the three-dimensional image data reconstructed by the image reconstruction circuit 17, transforms it into a more comprehensible form for the operator of the apparatus, and displays it on the image display device 18. The reconstruction process by the image reconstruction circuit 17 may be executed by a dedicated electronic circuit as shown in the drawing, or it may be executed by a software operation in a commonly available calculator, or a software operation in the calculator 11. The image reconstruction circuit 17 corresponds to the "generator" of the present invention. The image display device 18 corresponds to the "display unit" of the present invention.

As will be described later, the characteristic feature of the present invention lies in the position of the moving tables when photoacoustic signals are input, and the setting of the moving distance. The setting of these factors enables acquisition of photoacoustic signals at high speed, at an interval corresponding to a distance shorter than the array pitch between the receiving elements.

Figure 2:
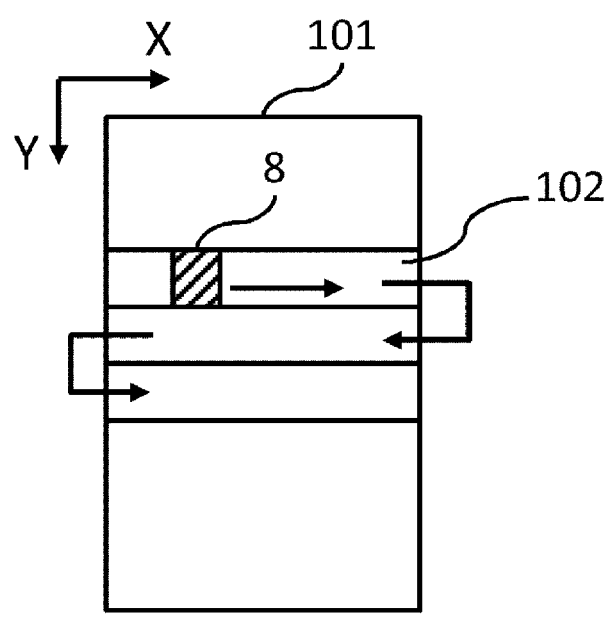
FIG. 2 is a diagram showing the steps of mechanical scanning of a wide area.

FIG. 2 shows specific steps of mechanical scanning of an examination area that is wider than the arrayed area of receiving elements of the probe 8. In the drawing, the examination area 101 is divided into a plurality of stripe regions 102. The probe 8 is moved continuously in each stripe region 102 and acquires photoacoustic signals. A three-dimensional image of a wide examination area can thus be generated. The stripe regions 102 may overlap each other in the Y direction. The same stripe region 102 may be scanned several times, and the reconstructed image may be averaged each time by performing averaging or the like, to improve the S/N ratio.

Figure 3:
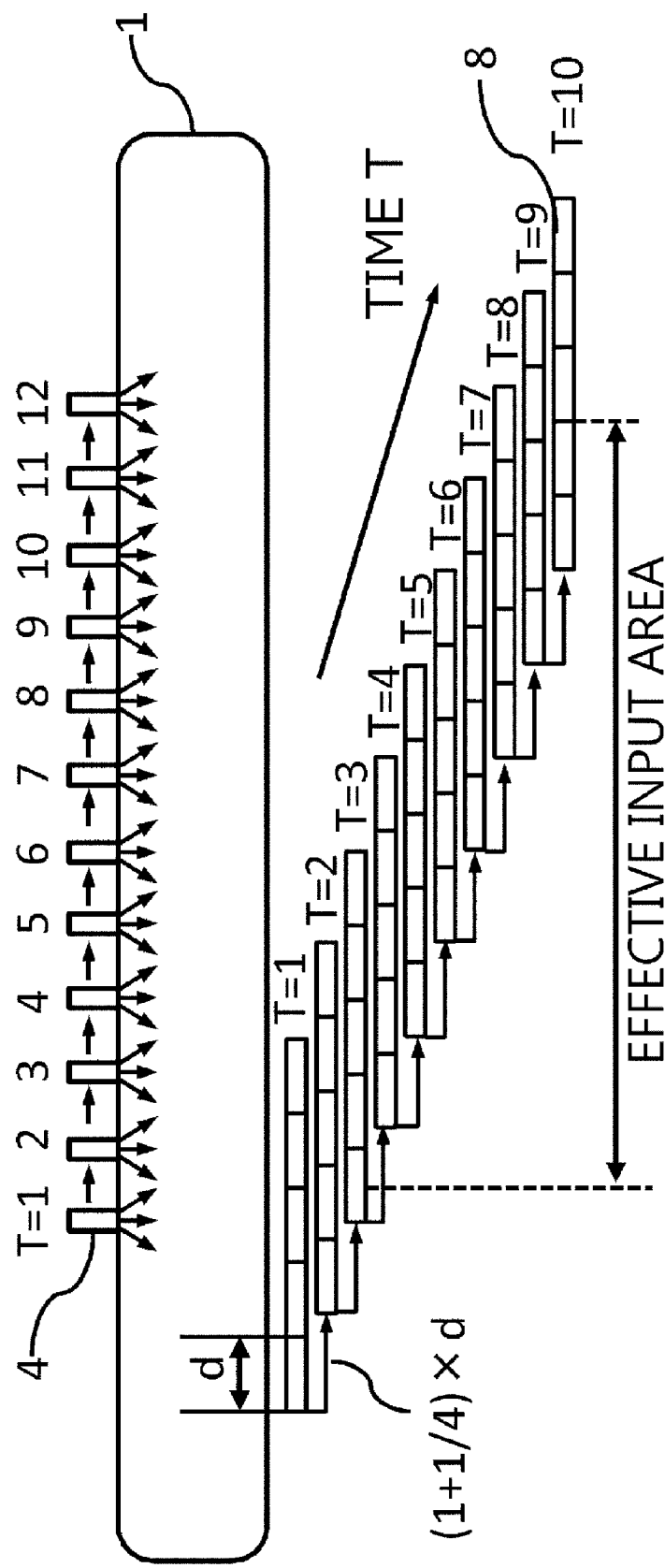
FIG. 3 is a diagram showing an example of moving table positions when acquiring photoacoustic signals.

FIG. 3 shows a specific example of setting of the moving table positions when detecting photoacoustic waves in accordance with the present invention. The drawing shows the positions of the probe 8 and the laser light source 4 relative to the object 1 at each laser emission timing (T=1, 2, 3, . . . ). The probe 8 in this example includes five receiving elements, which are arrayed equidistantly to each other by distance d.

The probe 8 is moved by $(1+¼)×d$ for each laser emission. If the laser pulse emission frequency is constant, the speed of moving the moving table can be made constant. If so, in the effective input area shown in the drawing, one of the receiving elements can receive a photoacoustic wave at an interval corresponding to a quarter of the array pitch d. In other words, even though the probe is moved continuously at constant speed, the photoacoustic signals can be acquired at an interval corresponding to a distance that is eventually shorter than the array pitch between receiving elements. Movement at constant speed can be controlled easily, and errors caused by mechanical vibration are reduced, so that photoacoustic signals with a better S/N ratio can be acquired.

Figure 4A:
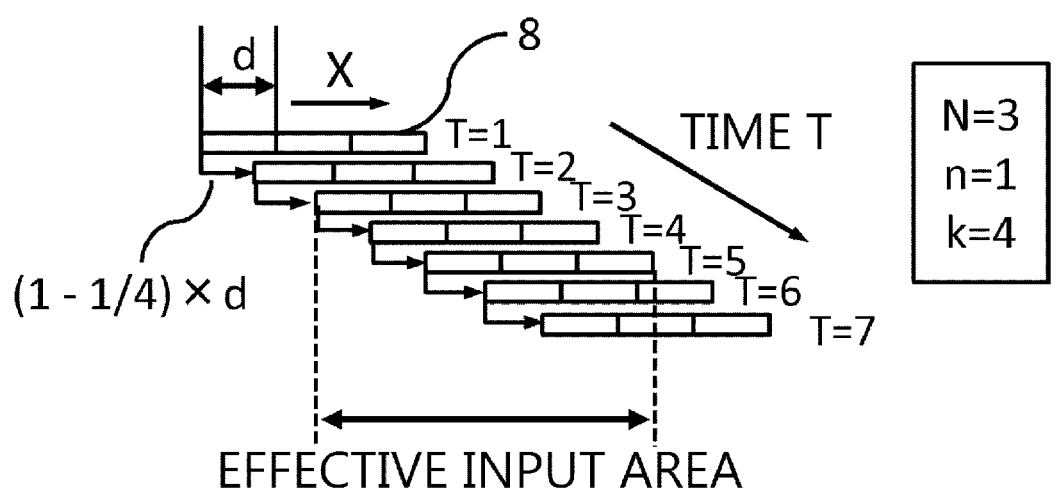
FIG. 4A is another diagram showing an example of moving table positions when acquiring photoacoustic signals.
Figure 4B:
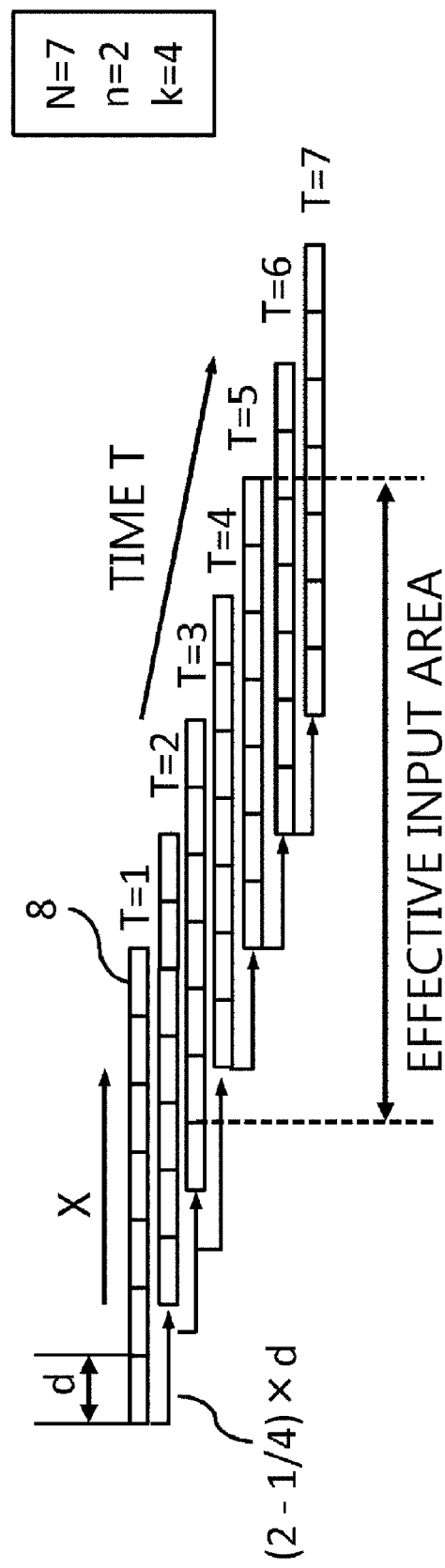
FIG. 4B is another diagram showing an example of moving table positions when acquiring photoacoustic signals.
Figure 4C:
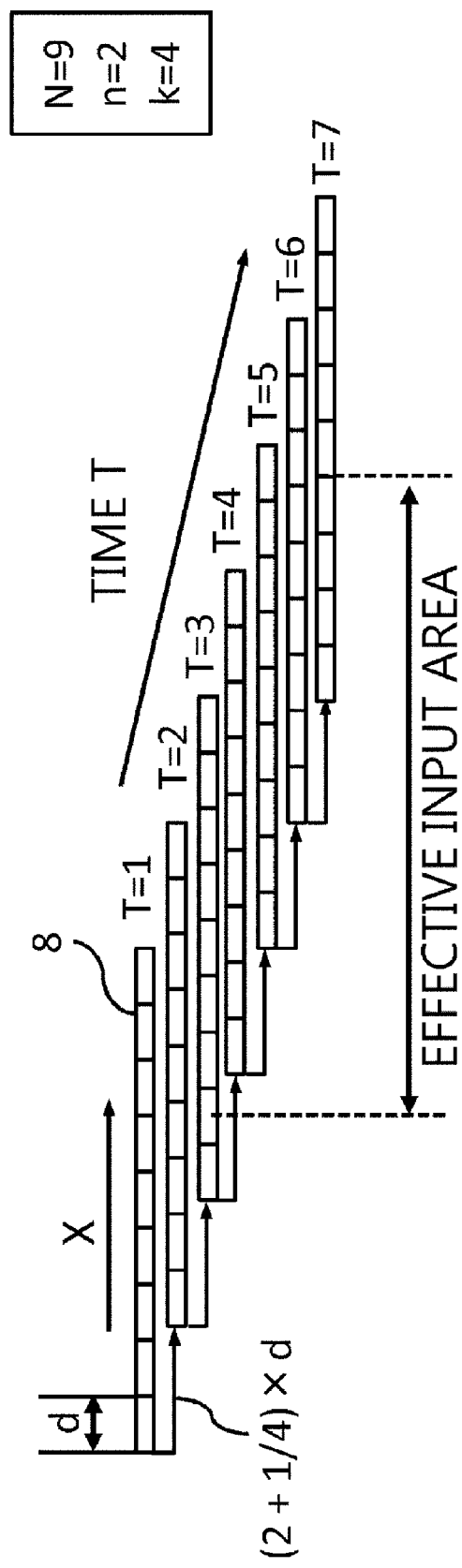
FIG. 4C is another diagram showing an example of moving table positions when acquiring photoacoustic signals.

FIG. 4A to FIG. 4C show methods of acquiring photoacoustic signals at a density that is four times higher than normally achieved, with the use of probes having different numbers of receiving elements from that of FIG. 3. In FIG. 4A, a probe with three elements is used. In this case, the moving distance for each laser emission is set $(1−¼)×d$, whereby photoacoustic signals can be acquired at a density that is four times higher than normally achieved while the probe is moved continuously at constant speed. In FIG. 4B, a probe with seven elements is used. In this case, the moving distance for each laser emission is set $(2−¼)×d$. In FIG. 4C, a probe with nine elements is used. In this case, the moving distance for each laser emission is set $(2+¼)×d$. In any of these cases, high density signal acquisition is possible with the use of a probe that is moving continuously at constant speed, similarly to the case described above.

According to the present invention, photoacoustic signals can be acquired at various densities with the use of a probe having various numbers of elements that is moved continuously at constant speed. FIG. 5 shows specific examples of optimal moving distances expressed with the array pitch d between elements as a unit and moving distances relative to emission frequency when acquiring photoacoustic signals at a density that is four times higher than normally achieved using a probe having a number N of arrayed elements. The speed and distance can be designed and controlled in a similar way for photoacoustic signal acquisition at other densities than a density four times higher than normally achieved.

Embodiment 2

Figure 6A:
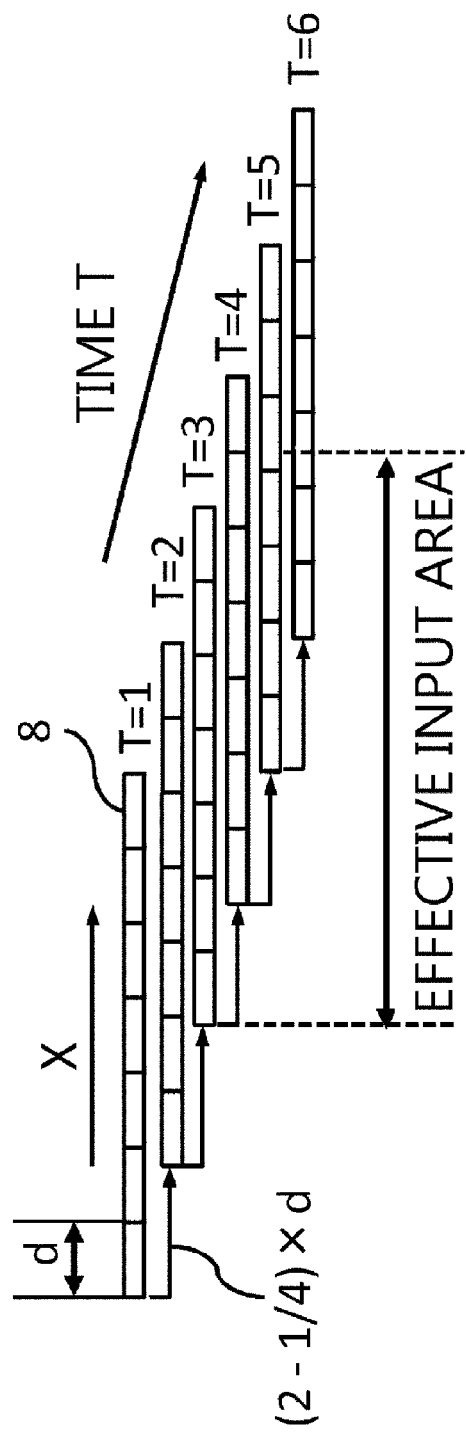
FIG. 6A is a diagram showing moving distances when inputting acoustic signals at various densities.
Figure 6B:
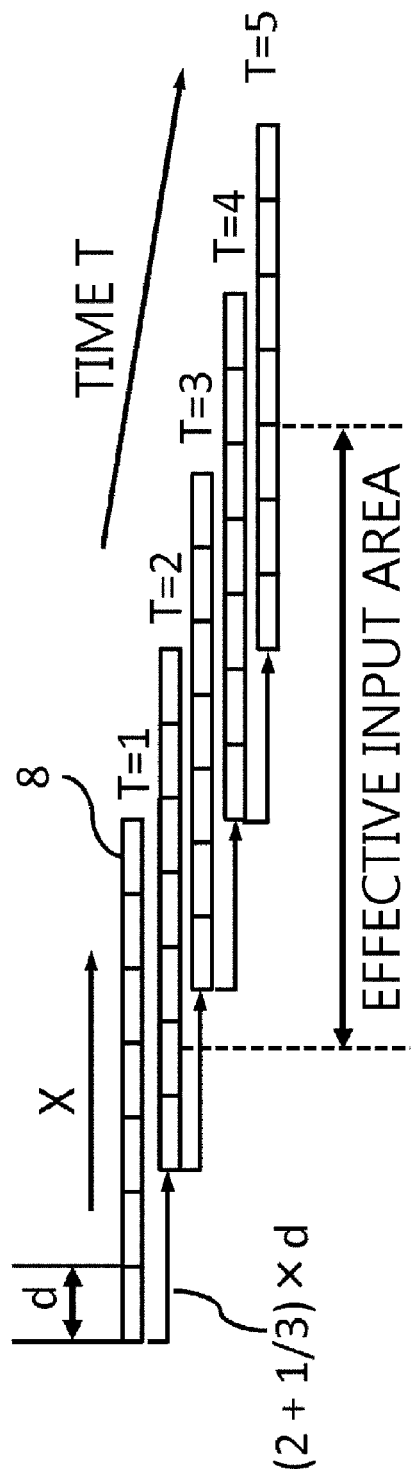
FIG. 6B is another diagram showing moving distances when inputting acoustic signals at various densities.
Figure 6C:
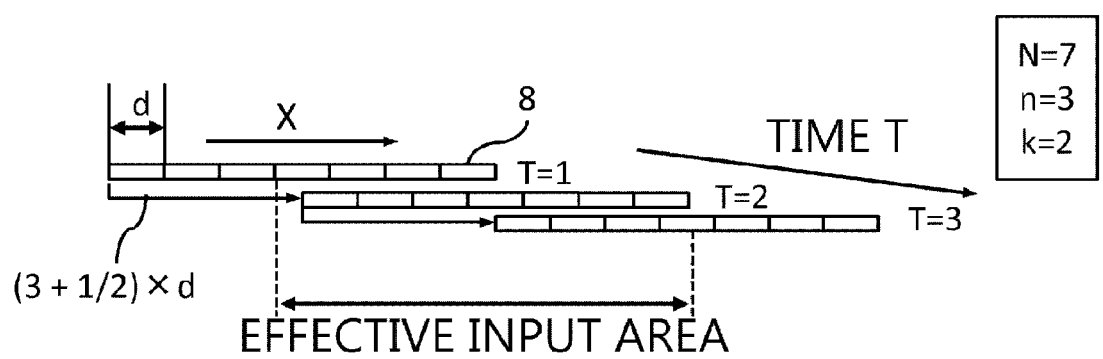
FIG. 6C is another diagram showing moving distances when inputting acoustic signals at various densities.

FIG. 6A to FIG. 6C show methods of acquiring photoacoustic signals at various densities with the use of a probe having seven receiving elements. In FIG. 6A, the moving distance for each laser emission is set $(2−¼)×d$. In this case, photoacoustic signals can be acquired at a density that is four times higher than normally achieved. In FIG. 6B, the moving distance is set $(2+⅓)×d$, whereby photoacoustic signals can be acquired at a density that is three times higher than normally achieved. In FIG. 6C, the moving distance is set $(3+½)×d$, whereby photoacoustic signals can be acquired at a density that is twice higher than normally achieved.

In this way, photoacoustic signal acquisition is possible at a short interval that corresponds to distance d/k, by setting the moving distance of a constant-speed, continuously moving probe to $(n±1/k)×d$, where n is an integer of 1 or more, and k is an integer of 2 or more. The integer k is defined in accordance with a desired signal density, and can also be understood as a division number.

Embodiment 3

FIG. 7 shows specific examples of division numbers k, optimal moving distances, and moving distances relative to emission frequency when the number of elements N is 13. The larger the division number k, the smaller the moving distance per emission frequency, but photoacoustic signals can be acquired at a k times density while moving the probe continuously at constant speed.

To carry out the present invention, it is important to calculate a specific value of optimal moving distance $(n±1/k)$ shown in FIG. 5 or FIG. 7, from the number N of arrayed receiving elements and the division number k. The optimal moving distance $(n±1/k)$ can be calculated by, for example, the sequence shown in FIG. 11. In FIG. 11, Floor [x] represents a function for determining a maximum integer not exceeding x.

The moving speed V of the probe in accordance with the present invention can be expressed by the following equation (1), where ΔT is the laser emission frequency and d is the array pitch between the probe elements:

$$V=(\text{optimal moving distance})×d/(\Delta T) \quad (1).$$

Thus, it can be seen that the moving speed of the moving tables may be set to the speed V obtained by equation (1) for inputting light-induced ultrasound signals at a density that is k times higher using a probe 8 having a number N of arrayed elements.

Conversely, a necessary number N of arrayed elements can be calculated from a division number k and moving distance for each laser emission $(n±1/k)$. Specifically, the number N of elements can be calculated by the following equation (2):

$$N=k×(n±1/k) \quad (2).$$

Thus, once a moving distance is calculated from a desired moving speed V and a division number k by equation (1), a minimum necessary number N of arrayed receiving elements can be readily determined based on this moving distance by equation (2). Namely, photoacoustic signals can be acquired at a desired moving speed V and with a division number k, with the use of a probe having an array of N or more receiving elements, where N is calculated by equation (2).

This can be rephrased as follows. To determine an effective input area, the probe needs a predetermined number or more of receiving elements along a first direction in accordance with its moving distance. The probe needs at least $(n×k+1)$ receiving elements, when the apparatus is controlled such that light is emitted from the light source each time the probe is moved by a distance that is $(n+1/k)$ times an array pitch d. Alternatively, the probe needs at least (n×k−1) receiving elements, when the apparatus is controlled such that light is emitted from the light source each time the probe is moved by a distance that is (n−1/k) times an array pitch d. In this way, photoacoustic signals can be acquired at short intervals without omission.

Embodiment 4

Figure 8:
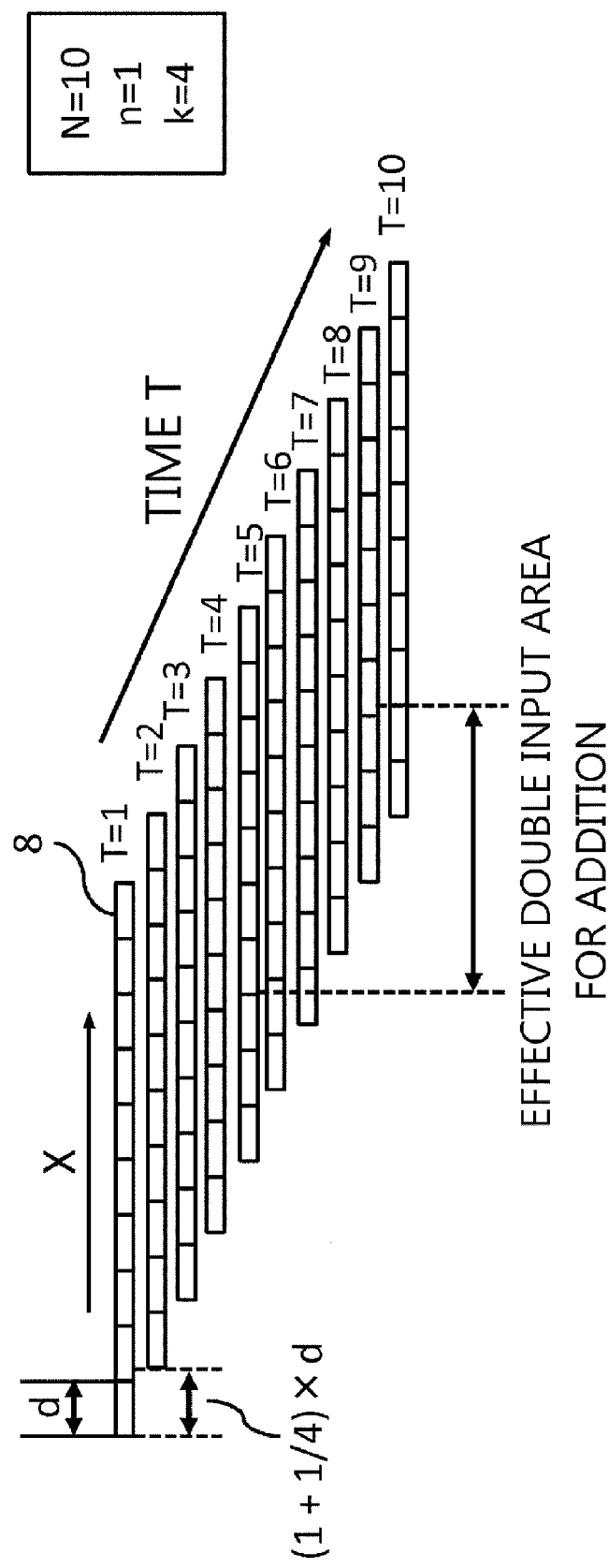
FIG. 8 is a diagram showing moving distances when a photoacoustic signal is input twice at the same position.

FIG. 8 shows signal acquisition when the number of receiving elements N is 10. The number of elements is twice that of the probe of FIG. 3. In this way, a photoacoustic signal originating from a photoacoustic wave generated from the same position on the object is input twice each within the effective input area as indicated in the drawing, so that the S/N ratio can be improved by an averaging process. Similarly, by increasing the number of receiving elements by M times, signal can be acquired M times from the same position, so that the S/N ratio can be further improved.

Embodiment 5

Figure 9A:
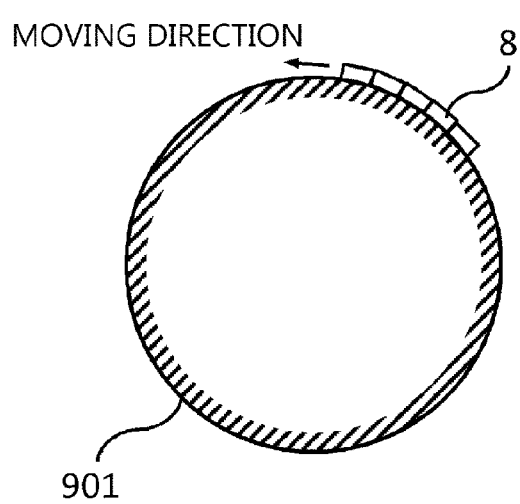
FIG. 9A and FIG. 9B are diagrams showing an example in which the probe is moved along the circumference of a circle.
Figure 9B:
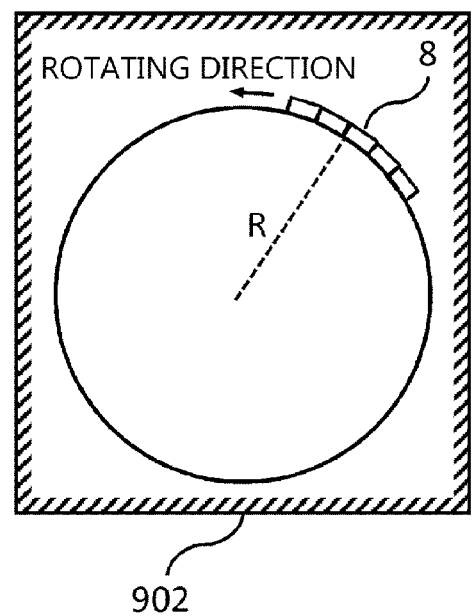

In the foregoing description, the probe is mechanically moved straight along the direction of arrangement of the receiving elements. FIG. 9 shows a case in which the probe is mechanically moved circularly. FIG. 9A shows a cylindrical object 901 scanned along its outer side. In this case, lateral cross-sectional images across the cylindrical object can be generated. FIG. 9B shows an object 902 scanned along a circle on the surface. In this case, cross-sectional images of a cylindrical body extending in the depth direction of the paper plane can be generated.

Variation Example

For ease of explanation, a one-dimensional probe having receiving elements arrayed along a first direction has been shown in the embodiments described above. The present invention, however, can also be applied to a two-dimensional probe having receiving elements arrayed two-dimensionally. The elements in this case would be arrayed also in a second direction intersecting (typically orthogonal to) the first direction. A two-dimensional probe can be considered as a plurality of one-dimensional probes operating in parallel. The object can be scanned over a wider area with such a two-dimensional probe.

The two-dimensional probe may be moved by (n±1/k) times the array pitch between receiving elements also in the second arrangement direction similarly to the first direction. By such control, photoacoustic signals can be acquired at an interval corresponding to 1/k of the array pitch between receiving elements also in the second direction.

The present invention can be applied also to probes having elements that do not closely adjoin each other but sparsely arranged, such as a sparse array design, by using the distance between the elements as d.

The light source need not be the pulsed laser as described above, and a device that generates other forms of radiation including microwave and LED light may be used.

Embodiment 6

The probe in the embodiments described above is configured to receive photoacoustic waves. Instead, a sound source may be used to transmit ultrasound to the object, and a sound wave reflected from the object (echo wave) may be detected. As long as the ultrasound source is fixed relative to the object, the detection target 6 always produces the same echo wave irrespective of the movement of the probe. Thus the present invention can be applied similarly to the case with photoacoustic waves. In this case, a single ultrasound source may be used, or a plurality of sound sources that operate in synchronism may be used.

The ultrasound source may be fixed to the moving probe, if it is of the type that generates a planar wave parallel to the moving direction of the probe. Also in this case, receiving elements at one point receive substantially the same acoustic wave irrespective of the movement of the probe, and so the present invention can be applied.

Figure 10:
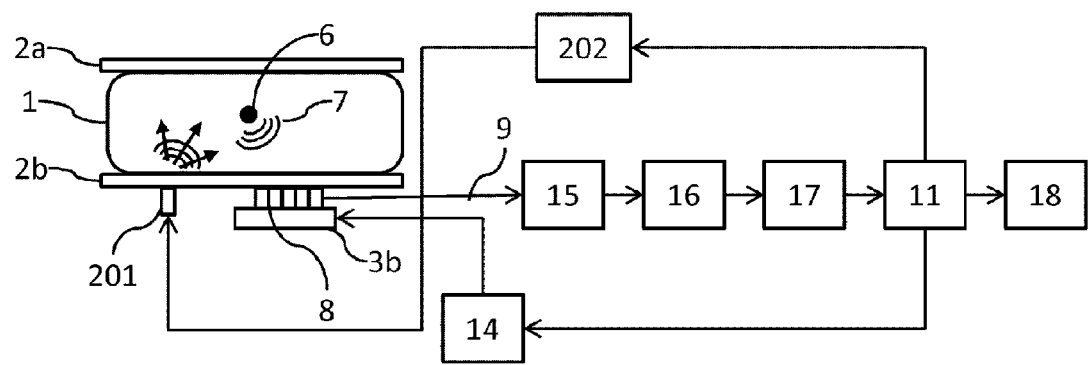
FIG. 10 is a diagram illustrating the configuration of an apparatus that emits ultrasound.

FIG. 10 shows the configuration of an ultrasonic imaging apparatus of this embodiment. Reference numeral 201 in the drawing denotes an ultrasound transmitter that generates pulses of ultrasound from a fixed position relative to the object. Reference numeral 202 denotes an ultrasound signal generation circuit that drives the ultrasound transmitter 201 for sending pulses of ultrasound from the ultrasound transmitter 201 into the object.

In this way, as the detection target 6 inside the object 1 always produces the same echo wave if the ultrasound transmitter 201 is in a fixed position relative to the object, the present invention can be applied and the effects described above can be achieved.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™) a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-073462, filed on Mar. 29, 2013, which is hereby incorporated by reference herein its entirety.

What is claimed is:

1. An object information acquiring apparatus, comprising:
a light source;
a probe having a plurality of receiving elements arrayed along a first direction, the receiving elements receiving an acoustic wave generated from an object when the object is irradiated with light from the light source, and converting the acoustic wave into an electrical signal;

a scanner moving the probe in the first direction; and
a controller controlling the light source and the scanner,
wherein the controller controls the apparatus such that light is emitted from the light source each time the probe is moved by a distance that is either (n+1/k) times or (n−1/k) times an array pitch between the receiving elements, where n is an integer equal to or greater than 1 and k is an integer equal to or greater than 2, while continuously moving the probe in the first direction.

2. The object information acquiring apparatus according to claim 1, wherein the scanner moves the probe at constant speed.

3. The object information acquiring apparatus according to claim 1, wherein
the probe has at least (n×k+1) receiving elements arrayed in the first direction, and
the controller controls the apparatus such that light is emitted from the light source each time the probe is moved by a distance that is (n+1/k) times an array pitch between the receiving elements.

4. The object information acquiring apparatus according to claim 1, wherein the probe has receiving elements arrayed also in a second direction intersecting the first direction.

5. The object information acquiring apparatus according to claim 1, further comprising:
an A/D converter that converts the electrical signal converted by the receiving elements into a digital signal;
a memory that stores the digital signal converted by the A/D converter; and
a generator that generates image data of inside of the object based on the digital signal stored in the memory.

6. The object information acquiring apparatus according to claim 1, wherein the controller moves the light source and the probe in synchronism with each other.

7. The object information acquiring apparatus according to claim 1, further comprising a display unit displaying an image based on image data generated by the generator.

8. The object information acquiring apparatus according to claim 1, wherein
the probe has at least (n+k−1) receiving elements arrayed in the first direction, and
the controller controls the apparatus such that light is emitted from the light source each time the probe is moved by a distance that is (n−1/k) times an array pitch between the receiving elements.

9. The object information acquiring apparatus according to claim 5, wherein the generator performs an averaging process on digital signals originating from acoustic waves received from a same position on the object, and generates image data of inside of the object based on the obtained signals.

10. The object information acquiring apparatus according to claim 1, wherein, where N is number of the plurality of receiving elements,
when a Floor function satisfies following relation, the controller sets n=Floor[(N+1)/k], and controls the apparatus such that light is emitted from the light source each time the probe is moved by a distance that is (n−1/k) times an array pitch between the receiving elements, and,
when the Floor function does not satisfy the following relation, the controller sets n=Floor[(N−1)/k], and, controls the apparatus such that light is emitted from the light source each time the probe is moved by a distance that is (n+1/k) times an array pitch between the receiving elements, the relation being:

(Floor[(N+1)/k+1/k)>(Floor[(N−1)/k+1/k).

11. An object information acquiring apparatus, comprising:
an ultrasound transmitter;
a probe having a plurality of receiving elements arrayed along a first direction, the receiving elements receiving an echo of a sound wave transmitted from the ultrasound transmitter to an object and reflected from the object, and converting the echo wave into an electrical signal;
a scanner moving the probe in the first direction; and
a controller controlling the ultrasound transmitter and the scanner,
wherein the controller controls the apparatus such that ultrasound is transmitted from the ultrasound transmitter each time the probe is moved by a distance that is (Floor[(N+1)/k+1/k) times an array pitch between the receiving elements when a Floor function satisfies following relation, and, controls the apparatus such that ultrasound is transmitted from the ultrasound transmitter each time the probe is moved by a distance that is (Floor[(N−1)/k+1/k) times an array pitch between the receiving elements when the Floor function does not satisfy the following relation, where k is an integer equal to or greater than 2 and N is number of the plurality of receiving elements, the relation being:

(Floor[(N+1)/k+1/k)>(Floor[(N−1)/k+1/k).

12. The object information acquiring apparatus according to claim 11, further comprising:
an A/D conversion step of converting the electrical signal converted in the previous step into a digital signal by the A/D converter;
a storage step of storing the digital signal converted in the A/D conversion step in the memory; and
a generation step of generating image data of inside of the object based on the digital signal stored in the storage step by the generator.

13. A method of controlling an object information acquiring apparatus that includes a light source, a probe having a plurality of receiving elements arrayed along a first direction, a scanner moving the probe in the first direction, a controller controlling the light source and the scanner, the method comprising:
a reception step of receiving an acoustic wave generated from an object when the object is irradiated with light from the light source and converting the acoustic wave into an electrical signal by the plurality of receiving element,
wherein, in the reception step, the controller controls the apparatus such that light is emitted from the light source each time the probe is moved by a distance that is either (n+1/k) times or (n−1/k) times an array pitch between the receiving elements, where n is an integer equal to or greater than 1 and k is an integer equal to or greater than 2 equal to or greater than 2, while continuously moving the probe in the first direction.

14. The method of controlling an object information acquiring apparatus according to claim 13, wherein the scanner continuously moves the probe.

15. The method of controlling an object information acquiring apparatus according to claim 13, wherein
the probe has at least (n+k−1) receiving elements arrayed in the first direction, and
the controller controls the apparatus such that light is emitted from the light source each time the probe is moved by a distance that is (n+1/k) times an array pitch between the receiving elements.

16. The method of controlling an object information acquiring apparatus according to claim 13, wherein
the probe has at least (n+k−1) receiving elements arrayed in the first direction, and
the controller controls the apparatus such that light is emitted from the light source each time the probe is moved by a distance that is (n−1/k) times an array pitch between the receiving elements.

17. The method of controlling an object information acquiring apparatus according to claim 13, wherein the probe has receiving elements arrayed also in a second direction intersecting the first direction.

18. The method of controlling an object information acquiring apparatus according to claim 13, wherein
the object information acquiring apparatus further comprises an A/D converter, a memory and a generator, and
the method further comprises:
an A/D conversion step of converting the electrical signal converted in the previous step into a digital signal by the A/D converter;
a storage step of storing the digital signal converted in the A/D conversion step in the memory; and
a generation step of generating image data of inside of the object based on the digital signal stored in the storage step by the generator.

19. The method of controlling an object information acquiring apparatus according to claim 18, wherein the generator performs an averaging process on digital signals originating from acoustic waves received from a same position on the object, and generates image data of inside of the object based on the obtained signals.

20. The method of controlling an object information acquiring apparatus according to claim 13, wherein the controller moves the light source and the probe in synchronism with each other.

21. The method of controlling an object information acquiring apparatus according to claim 13, wherein
the object information acquiring apparatus further comprises a display unit, and
the method further comprises a displaying step of displaying image based on the image data generated by the generator.

22. A method of controlling an object information acquiring apparatus that includes an ultrasound transmitter, a probe having a plurality of receiving elements arrayed along a first direction, a scanner moving the probe in the first direction, and a controller controlling the ultrasound transmitter and the scanner, the method comprising:
a transmission step of transmitting an ultrasound wave to an object by using the ultrasound transmitter; and
a reception step of receiving an echo wave reflected within the object and converting the echo wave into an electrical signal by using the plurality of receiving elements,
wherein the controller controls the apparatus such that ultrasound is transmitted from the ultrasound transmitter each time the probe is moved by a distance that is (Floor[(N+1)/k+1/k) times an array pitch between the receiving elements when a Floor function satisfies following equation, and, controls the apparatus such that ultrasound is transmitted from the ultrasound transmitter each time the probe is moved by a distance that is (Floor[(N−1)/k+1/k) times an array pitch between the receiving elements when the Floor function does not satisfy the following equation, where k is an integer equal to or greater than 2 and N is number of the plurality of receiving elements:

$$(\text{Floor}[(N+1)/k+1/k]) > (\text{Floor}[(N-1)/k+1/k]) \quad \text{(equation)}.$$

23. The method of controlling an object information acquiring apparatus according to claim 22, wherein the object information acquiring apparatus further comprises:
an A/D converter converting the electrical signal converted by the receiving elements into a digital signal;
a memory storing the digital signal converted by the A/D converter; and
a generator generating image data of inside of the object based on the digital signal stored in the memory.

* * * * *